US007809431B2

(12) United States Patent
Texier-Nogues et al.

(10) Patent No.: US 7,809,431 B2
(45) Date of Patent: Oct. 5, 2010

(54) METHOD OF OPTICALLY IMAGING BIOLOGICAL TISSUES BY USING FLUORESCENCE, IN PARTICULAR FOR DEFINING REGIONS OF INTEREST IN TISSUES TO BE ANALYZED BY TOMOGRAPHY

(75) Inventors: Isabelle Texier-Nogues, Grenoble (FR);
Philippe Peltie, Saint Paul de Varces (FR); Emilie Heinrich, Sassenage (FR); Rolande Blanc, Noyarey (FR)

(73) Assignee: Commissariat a l'Energie Atomique, Paris (FR)

( * ) Notice: Subject to any disclaimer, the term of this patent is extended or adjusted under 35 U.S.C. 154(b) by 578 days.

(21) Appl. No.: 11/736,333

(22) Filed: Apr. 17, 2007

(65) Prior Publication Data
US 2007/0249943 A1 Oct. 25, 2007

(30) Foreign Application Priority Data
Apr. 24, 2006 (FR) .................................. 06 03610

(51) Int. Cl.
*A61B 6/00* (2006.01)
(52) U.S. Cl. ...................................... 600/476; 600/473
(58) Field of Classification Search ................... 600/407, 600/473–478
See application file for complete search history.

(56) References Cited

U.S. PATENT DOCUMENTS

| 4,215,275 A | * | 7/1980 | Wickersheim ............... 374/137 |
| 4,541,438 A | | 9/1985 | Parker et al. |
| 4,852,579 A | | 8/1989 | Gilstad et al. |
| 5,370,119 A | * | 12/1994 | Mordon et al. ............... 600/431 |
| 5,452,717 A | * | 9/1995 | Branigan et al. ............ 600/323 |
| 5,697,373 A | | 12/1997 | Richards-Kortum et al. |
| 6,424,857 B1 | * | 7/2002 | Henrichs et al. ............ 600/431 |
| 2003/0013973 A1 | | 1/2003 | Georgakoudi et al. |

* cited by examiner

*Primary Examiner*—Long V Le
*Assistant Examiner*—Nigel Fontenot
(74) *Attorney, Agent, or Firm*—Oblon, Spivak, McClelland, Maier & Neustadt, L.L.P.

(57) ABSTRACT

The present invention relates to a method of optically imaging at least one biological tissue, in particular to define areas of interest of tissue(s) to be analyzed by tomography.

The method according to the invention comprises the following steps:
a) introducing at least one fluorescent marker into the tissue(s);
b) exciting the marker by incident light and detecting emission bands relating to fluorescence emitted by the marker in response to that excitation; then
c) analyzing the fluorescence in these emission bands; and the step b) comprising:
sequentially exciting said marker at n different incident excitation wavelengths $\lambda_i$, said marker being adapted to be excited by at least two of the wavelengths $\lambda_i$ and to emit in response to each wavelength $\lambda_i$ a series $S_i$ of m simultaneous emission bands $B_j$ having different maximum wavelengths $\lambda'_j$ that are substantially the same from one series $S_i$ to another; and
detecting these series $S_i$ in order to deduce therefrom an estimate of the three-dimensional location of said marker in the tissue(s) and/or the mean absorption coefficients of the tissue(s) for the excitation wavelengths $\lambda_i$.

19 Claims, 7 Drawing Sheets

Depth 2mm - NG: 879

10%/1 Solution in a capillary

Depth 3mm - NG: 309

Depth 4mm - NG: 220

10%/1 Solution in a capillary

Depth 2mm NG: 223

Powder in capillary

Depth 2mm NG: 533

Powder in capillary

Depth 3mm NG: 260

METHOD OF OPTICALLY IMAGING BIOLOGICAL TISSUES BY USING FLUORESCENCE, IN PARTICULAR FOR DEFINING REGIONS OF INTEREST IN TISSUES TO BE ANALYZED BY TOMOGRAPHY

The present invention relates to a method of optically imaging at least one biological tissue by using fluorescence, in particular for defining regions of interest of tissue(s) to be analyzed by tomography. The invention applies more particularly to tissues in vivo.

BACKGROUND OF THE INVENTION

Optical imaging by fluorescence complements the various types of nuclear medical instruments, such as those using positron emission tomography (PET), gammatomography (SPECT, i.e. monophotonic emission tomography), X-ray imaging (e.g. digital radiography, X-ray tomography) and MRI (magnetic resonance imaging).

Optical imaging using fluorescence requires the injection into a human or animal organism of a marker (e.g. an antibody/fluorophore conjugate) that specifically targets an area of interest to the biologist or doctor, for example a malignant tumor of an organ. Below, "fluorophore" means any molecular or particulate structure able to emit light in response to luminous excitation (e.g. organic fluorophores, semiconductor nanocrystals, quantum boxes, etc.), and "marker" means the injected substance comprising such a fluorophore.

It is therefore possible to detect cancerous nodules by a technique that is much less invasive and destructive than ionizing radiation imaging (e.g. imaging using X-rays or radioactive tracers). Moreover, optical imaging systems offer good resolution at millimeter scale.

Finally, it should be noted that the equipment necessary for such optical imaging is relatively simple, comprising in particular a light source in the form of a compact laser diode, a detector in the form of a high-sensitivity camera, and motorized tables, and is of a very much lower cost than imaging equipment using ionizing radiation.

The simplest imaging systems using fluorescence include a light source (e.g. of fiber, laser, arc lamp, light-emitting diode type) and a filtered camera (filtered to avoid backscattering of the excitation light) for acquiring a fluorescent image; this is known as fluorescence reflectance imaging (FRI). The photons penetrate only a small distance (approximately 1 millimeter (mm) into the tissue and this technique can locate only markers on the surface of the tissue (e.g. only marked surface tumors in oncology).

If the marker (e.g. the marked tumor) is deep (for example 1 centimeter (cm) deep), it is impossible to locate it using FRI type acquisition alone, because of strong diffusion of the excitation photons and because of the photons emitted by the fluorophore. The light source is therefore moved, to "grid" the area to be analyzed and acquire as many images as possible of the light source. A complex reconstruction process based on all of the acquired images reconstructs the fluorescent image in "3D": this is known as optical tomography. Small animals such as rats or mice can be imaged using a device of this kind.

When optically imaging the entire body of a small animal, it is generally possible either:

to acquire a global fluorescent image in two dimensions in a few seconds at most using the FRI technique, with the drawback of having no information as to depth in the tissue; or to use the tomography technique, which produces an image in three dimensions but which requires, firstly, a series of images captured for respective different source/detector positions (acquisition time from 10 to 15 minutes for a field of approximately 1 cm$^2$ and a step size of 2 mm) and, secondly, image reconstruction algorithms, with reconstruction time being proportional to the size of the area to be reconstructed. The difficulty encountered in "3D" reconstruction by tomography when a fluorophore is used therefore lies in the lack of information on the restricted area in which the markers are likely to be found (these markers are generally fixed to the organ to be observed, such as a malignant tumor, for example). It is then necessary to scan the whole of the object for imaging (for a mouse the total area is 50×75 mm$^2$), with a step size of a few millimeters to avoid excessively long acquisition times, and information is lost between the excitation points.

Moreover, image reconstruction algorithms usually start from a homogeneous distribution of sources of fluorescence in the entire body of the animal (i.e. the same, zero or non-zero, level of fluorescence). This therefore requires a large number of iterations before converging towards a reliable distribution of the sources of fluorescence and can therefore cause errors.

The excitation wavelength used is usually from 600 nanometer (nm) to 800 nm and the fluorophores (typically Cy5, Cy7, Alexa 633 or Alexa 750 cyanines) emit at wavelengths from 700 nm to 900 nm. In this range of wavelengths, autofluorescence of biological tissue is reduced compared to the bluegreen range (from 400 nm to 500 nm), but this undesirable autofluorescence is nevertheless always present (autofluorescence of biological tissue is caused by the presence of endogenous chromophores, such as porphyrines in haemoglobin, fluorescent proteins, etc.). Furthermore, with a fluorophore fixed to the organ to be detected, there is the drawback of the signal/noise ratio being relatively low.

A major drawback of those prior art optical imaging techniques using fluorescence is therefore essentially, with the FRI technique, the absence of depth information for locating the marker in the organ to be imaged and, with tomography, the difficulty of obtaining satisfactory depth (direction Z) information in addition to information relating to the surface of the organ (directions X and Y).

The paper "A dual fluorochrome probe for imaging proteases", M. F. Kircher, R. Weissleder, L. Josephson, Bioconj. Chem. 2004, 15, 242 describes an optical imaging method using a dual marker formed of a nanoparticle functionalized by two organic fluorophores (Cy5.5 and Cy7 cyanines) to evaluate the activity of an enzyme in tissue. The ratio of the emissions from those two fluorophores is calculated to estimate the location in depth of the marked vector in the tissue. The marker is either excited at $\lambda_1$=630 nm and analyzed at $\lambda'_1$=700 nm for the Cy5.5 fluorophore, or excited at $\lambda_2$=736 nm and analyzed at $\lambda'_2$=800 nm for the Cy7 fluorophore, in accordance with the acquisition set-up illustrated in the appended FIG. 1, which shows that to each excitation wavelength $\lambda_1$, $\lambda_2$ there corresponds one and only one narrow spectral band around a wavelength $\lambda'_1$ or $\lambda'_2$ of maximum fluorescence A major drawback of that optical imaging method using a dual marker is the complexity of fabrication of the marker, because of the operation of grafting the two fluorophores onto the same vector.

Another drawback of that method is that the relatively wide absorption/emission spectra of those two fluorophores overlap, which generates filtering difficulties for detecting each of the two fluorophores separately in order to be able to preserve the ratio of the two emissions yielding the estimate of the depth in the tissue. Moreover, the proximity of the absorption and emission wavelengths of the two markers generates spurious phenomena such as energy transfer and inhibition of fluorescence.

Another drawback of that method is that the emission spectrum of those two markers based on organic fluorophores can be offset because of interactions with the biological environment.

A final drawback of that dual marker method is that the use of the ratio of the intensity of the emissions of fluorescence of the two fluorophores to estimate the depth of the marker relies on two assumptions that are open to challenge, i.e. that the respective absorption coefficients $a_1$ and $a_2$ of the tissue at the two excitation wavelengths $\lambda_1$ and $\lambda_2$ are the same, as are the respective absorption coefficients $a'_1$ and $a'_2$ of the tissue at the emission wavelengths $\lambda'_1$ and $\lambda'_2$ (i.e. $a_1=a_2$ and $a'_1=a'_2$). These two assumptions are justified in the above publication by the mutual proximity firstly of the wavelengths $\lambda_1$ and $\lambda_2$, and secondly of the wavelengths $\lambda'_1$ and $\lambda'_2$. However, that proximity of the excitation and emission wavelengths of the two fluorophores used is found to penalize the optical filtering for measuring the fluorescence ratio, which degrades the quality with which the depth of the marker is evaluated in the tissue.

U.S. Pat. No. 5,370,119 describes a method of measuring the pH of an appropriate target that produces information as to the evolution of pH over time (its kinetic profile), comprising:
    bringing the target to be analyzed into contact with a fluorescent marker having at least two excitation peaks and only one emission peak, with the emission spectrum being dependent on pH;
    successively exciting the target treated in this way at the excitation wavelengths of the fluorescent marker; and
    measuring the fluorescence emitted by the target at those excitation wavelengths and calculating the pH of the target from the ratio of the fluorescence signals emitted in response to the two excitation wavelengths by reading off the pH corresponding to the ratio obtained on a calibration curve for the marker, giving the ratio as a function of pH.

Note that fluorescent markers of the organic fluorophore type such as fluoroscein used in the above document are not able to emit at a plurality of emission wavelengths in response to the plurality of excitation wavelengths, but at one and only one emission wavelength.

Note further that the measurement method of the above document does not provide an estimate of the three-dimensional location of the marker in the tissue or of the mean absorption coefficients of the tissue in relation to the excitation wavelengths.

OBJECTS AND SUMMARY OF THE INVENTION

An object of the present invention is to propose a method of optically imaging at least one biological tissue, the method comprising the following steps:
    a) introducing at least one fluorescent marker into said at least one tissue;
    b) exciting said at least one marker by incident light radiations and detecting bands of emission relating to fluorescence emitted by said at least one marker in response to that excitation; then
    c) analyzing the intensities of fluorescence relative to said emission bands;
    thereby removing the drawbacks mentioned above.

To this end, in the method of the invention the step b) comprises:
    sequentially exciting said at least one marker at n different incident excitation wavelengths $\lambda_i$, said at least one marker being adapted to be excited by at least two of these n wavelengths $\lambda_i$ and to emit in response to each wavelength $\lambda_i$ a series $S_i$ of m simultaneous emission bands $B_j$ having different maximum wavelengths $\lambda'_j$ that are substantially the same from one series $S_i$ to another (where n and m are independent integers equal to or greater than 2 and where i and j respectively vary from 1 to n and from 1 to m ); and
    detecting at least two of these series $S_i$ that each comprise these m bands $B_j$ emitted simultaneously in order to deduce therefrom in the step c) an estimate of the three-dimensional location of said marker in the tissue(s) and/or the mean absorption coefficients of the tissue(s) for the excitation wavelengths $\lambda_i$.

According to another feature of the invention, said at least one marker may be based on a fluorophore or a group of fluorophores that is adapted to be excited by these wavelengths $\lambda_i$ and, in response to each of them, to emit these m bands $B_j$ simultaneously.

Note that the optical imaging method of the invention defines areas of interest of the tissue to be imaged more deeply by tomography in an acquisition time that is relatively short because of the estimate of the three-dimensional location arrived at by obtaining much more information on the tissue than a simple image obtained by the FRI optical imaging method, in particular by means of the detection in depth (in the direction Z) of the or each marker in the tissue in addition to the two surface directions X and Y accessible by FRI imaging.

Note also that this method of the invention provides information as to the mean absorption coefficients of the tissue.

Accordingly, by using judiciously selected markers, the method of the invention provides a simple way to obtain an advantageous starting point for algorithms for reconstructing images of entire bodies of animals by improving the quality of reconstruction at the same time as reducing the acquisition time. In fact, in contrast to traditional reconstruction algorithms that use tabulated absorption coefficients and the a priori assumption of a homogeneous distribution of the sources of fluorescence in each animal (which are generally selected to be the same from one animal to another), the method of the invention uses by way of its starting point for reconstruction an image that is specific to each animal and that already contains three-dimensional information and mean values of the absorption coefficients of the tissue relating to the animal under examination.

In known manner, in the present description "absorption map" means the map of attenuation of the tissue at the excitation wavelength in transmission mode (with the light source on one side of the object to be examined and the detector camera on the other side).

In known manner, "emission map" means the fluorescent image of the tissue when it is excited at a given wavelength and the signal is collected at one or more other wavelengths.

In known manner, "backscattering map" means the map of scattering from the tissue at the excitation wavelength (with the light source and the detector camera then both being on the same side of the object to be examined).

According to another feature of the invention, step c) may also comprise determining one or more emission ratio(s) between the m maximum wavelengths $\lambda'_j$ and one or more transmission ratio(s) of the or each tissue between the n excitation wavelengths $\lambda_i$ to obtain an emission map of the or each tissue.

An embodiment of the invention uses an optical imaging device of the type operating in transmission mode and including a source of said incident radiations and a detector that are situated on respective both opposite sides of the or each tissue to be imaged.

A different embodiment of the invention uses an optical imaging device including a source of said incident radiations and a detector, both of which are situated on the same side of the tissue to be imaged. Step b) then advantageously also deduces a backscattering map of the tissue at the n excitation wavelengths $\lambda_i$.

The n excitation wavelengths $\lambda_i$ are preferably offset in pairs by an interval of at least 100 nm and even more preferably of at least 150 nm.

The m maximum wavelengths $\lambda'_j$ of said emission bands $B_j$ are preferably offset in pairs by an interval of at least 100 nm.

The n excitation wavelengths $\lambda_i$ are advantageously all of between 750 nm and 1000 nm.

The m maximum wavelengths $\lambda'_j$ of said emission bands $B_j$ are advantageously all of between 450 nm and 800 nm.

In a preferred embodiment of the invention the step b) comprises:

successively exciting said marker at two different excitation wavelengths $\lambda_1$ and $\lambda_2$, said marker being adapted to be excited by the two wavelengths $\lambda_1$ and $\lambda_2$ and to emit in response substantially the same series $S_1$, $S_2$ of two emission bands $B_1$ and $B_2$ having respective different maximum wavelengths $\lambda'_1$ and $\lambda'_2$ (n =m =2); and detecting the two series $S_1$, $S_2$, each comprising the two bands $B_1$ and $B_2$ emitted simultaneously.

According to this preferred embodiment, said at least one marker is advantageously based on a fluorophore or a group of fluorophores that is adapted to be excited by these two wavelengths $\lambda_1$ and $\lambda_2$ and, in response to each of them, to emit the two bands $B_1$ and $B_2$ simultaneously.

According to another feature of the invention the marker may advantageously comprise a fluorophore based on an inorganic up-converting semiconductor nanocrystal.

Said nanocrystal may advantageously then include:

an oxide or an oxysulfide of a metal chosen from the group consisting of yttrium, vanadium, and the rare earths (i.e. by definition an element from the table of the elements having an atomic number from 57 to 71, e.g. gadolinium); and an emitter ion, such as a cation of a rare earth metal such as terbium, erbium, or europium.

The absorber that said nanocrystal may further include may itself be in the form of an ion, for example an ytterbium ion.

Even more advantageously, said nanocrystal may be based on an yttrium oxide having the formula $Y_2O_3$: $Er^{3+}$, $Yb^{3+}$, where Er and Yb are respectively erbium and ytterbium and each is present in said nanocrystal at a doping rate from 1% to 20%.

Note that the usual markers, whether based on organic fluorophores or on semiconductor inorganic nanocrystals (i.e. "quantum dots") that are to the contrary of the down-converting nanocrystal type, are known to emit at only one wavelength and are therefore not usable in the method of the present invention.

Note also that these up-converting nanocrystals absorb photons of low energy (typically in the infrared spectrum) and emit photons of higher energy (typically in the visible spectrum), which makes these nanocrystals very advantageous as markers for optical imaging of small animals in vivo. In effect, these nanocrystals are resistant to photon-bleaching, they emit at wavelengths at which the phenomena of autofluorescence are minimized or avoided (because these undesirable processes always take place at a longer wavelength than the excitation wavelength), and they have very narrow-band emission spectra.

Note, however, that new fluorophores other than these up-converting inorganic nanocrystals could be usable in the method of the invention provided that they can be excited by at least two different excitation wavelengths $\lambda_i$ and they emit simultaneously in response to each of them at two or more different emission wavelengths $\lambda'_i$.

Said tissue imaged by the method of the invention is advantageously of the in vivo type, said or each marker being based on a fluorophore/biological ligand conjugate, such as an up-converting semiconductor functionalized inorganic nanocrystal/biomolecule conjugate, which may be a peptide, an oligonucleotide, DNA, a protein, etc.

These functionalized nanocrystals may be obtained, for example, by the functionalization method described in the document FR-A-2 812 662 in the name of the Applicant, which describes the use of epoxy silane to obtain a diol function that can then be activated in aldehyde to react with amine functions of biomolecules.

Note that the markers usable in the method of the invention may have other properties useful in imaging, in addition to the above-mentioned optical properties. In particular they may consist of or be linked to:

MRI contrast agents, for example chelates of gadolinium or nanoparticles of oxides of iron or gadolinium (they may equally include a core of iron or gadolinium oxide); and contrast agents for PET, SPECT, X-ray or any other type of imaging.

Accordingly, said or each marker of the invention may further comprise at least one element, selected for example from the group consisting of chelates of gadolinium, nanoparticles of oxides of iron and nanoparticles of gadolinium, which is adapted to make said marker act as a contrast agent having another non-optical property usable in the above-mentioned imaging techniques, for example.

Note further that the markers usable in the method of the invention may consist of a single entity having the required optical properties, or a set of such entities assembled into a nanostructure so as to constitute a library of different markers that can be detected simultaneously or separately.

As indicated above, an emission and/or absorption and/or backscattering map specifically obtained in the step c) may be used to define at least one region of interest of said or of each tissue to be analyzed by tomography and this definition of said or each region of interest specific to said tissue is advantageously used as a starting point for image reconstruction by tomography.

Even more advantageously, said map(s) relate(s) to an entire animal body.

BRIEF DESCRIPTION OF THE DRAWINGS

The above-mentioned features of the present invention, and others, can be better understood on reading the following description of embodiments of the invention, given by way of illustrative and non-limiting example, said description referring to the appended drawings, in which.

MORE DETAILED DESCRIPTION

Figure 1:
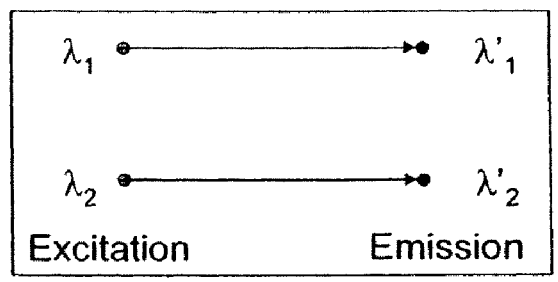
FIG. 1 is a diagram illustrating symbolically a prior art principle of image acquisition relating to a dual marker optical imaging method.
Figure 2:
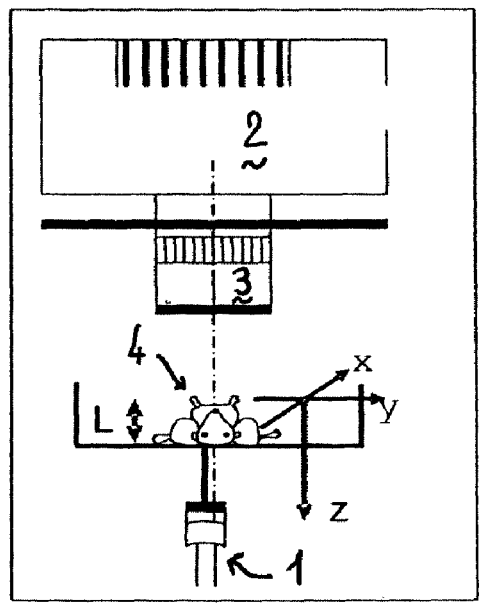
FIG. 2 is a diagrammatic view in profile of a tomography installation configured in transmission mode which can be used to implement the optical imaging method of the invention.

As shown in FIG. 2, all the examples and trials described below used an experimental tomography system configured in transmission mode, and including a laser light source 1 emitting in the near infrared spectrum and a high-sensitivity detection camera 2 provided with a lens 3 respectively situated in front of and behind a small animal 4 to be imaged (for example a mouse).

Emission maps acquired in transmission mode and absorption maps were used in particular. This system could also have the light source 1 on the same side of the animal 4 as the camera 2, in which case emission and backscattering maps would be used.

1) Detailed Description of the Method of the Invention:

In FIG. 2, L designates the total thickness of the animal, assumed to be known and measured by another device, and z designates the depth of the fluorophores in the direction Z of the animal 4 (X and Y being two directions on the surface of the animal 4). The luminous intensity signals I $(\lambda_1, \lambda'_1)$ et I $(\lambda_2, \lambda'_2)$ were measured with excitation at $\lambda_1$ and $\lambda_2$ and detection at $\lambda'_1$ and $\lambda'_2$ for both $\lambda_1$ and $\lambda_2$.

The transmission of light is given in known manner by I $(\lambda_1) = I_0 (\lambda_1) e^{-a_1 z}$ and I $(\lambda_2) = I_0 (\lambda_2) e^{-a_2 z}$, where $a_1$ and $a_2$ respectively represent the mean coefficients of absorption of the tissue at $\lambda_1$ and $\lambda_2$, $I_0$ the incident intensity, and z the distance traveled in the tissue. If, to simplify the problem, only absorption by the tissue is considered and diffusion is ignored, there are five unknowns:

the depth of the fluorophore in direction Z; and
the coefficients of absorption $a_1, a_2, a'_1, a'_2$ of the tissue at the respective wavelengths $\lambda_1, \lambda_2, \lambda'_1, \lambda'_2$.

The quantum efficiencies of fluorescence of the fluorophores are denoted $\eta(\lambda_1, \lambda'_1), \eta(\lambda_1, \lambda'_2), \eta(\lambda_2, \lambda'_1)$ and $\eta(\lambda_2, \lambda'_2)$ These quantum efficiencies can be measured independently by means of a spectrophotometer.

Thus five equations are needed to solve the system.

Figure 3:
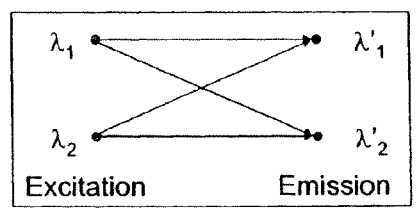
FIG. 3 is a diagram illustrating symbolically the principle of image acquisition in accordance with a preferred embodiment of the optical imaging method of the invention.

FIG. 3 shows a preferred example of the detection principle that characterizes the imaging method of the invention, whereby:

a single fluorophore has the property of emitting simultaneously at at least two different wavelengths $\lambda'_1$ and $\lambda'_2$ when it is excited at a given wavelength $\lambda_1$ or $\lambda_2$ (producing an emission map); and the same fluorophore is excited at at least two different wavelengths $\lambda_1$ and $\lambda_2$ (producing backscattering and/or absorption maps).

By acquiring four or six images corresponding to transmission at $\lambda_1$ and $\lambda_2$ and to emission at $\lambda_1/(\lambda'_1$ and $\lambda'_2), \lambda_2/(\lambda'_1$ and $\lambda'_2)$, or $\lambda_1/\lambda'_1, \lambda_1/\lambda'_2, \lambda_2/\lambda'_1, \lambda_2/\lambda'_2$ (or more images if more excitation and/or emission wavelengths are envisaged), it is possible quickly and easily, firstly, to define areas of interest to be imaged at greater depth by tomography by producing an absorption, backscattering, or emission map and, secondly, to supply as the starting point for image reconstruction by tomography a distribution of the sources of fluorescence in the animal with an image specific to each animal and already including information in respect of the directions X, Y, Z. This improves the speed and the accuracy of image reconstruction.

Figure 4:
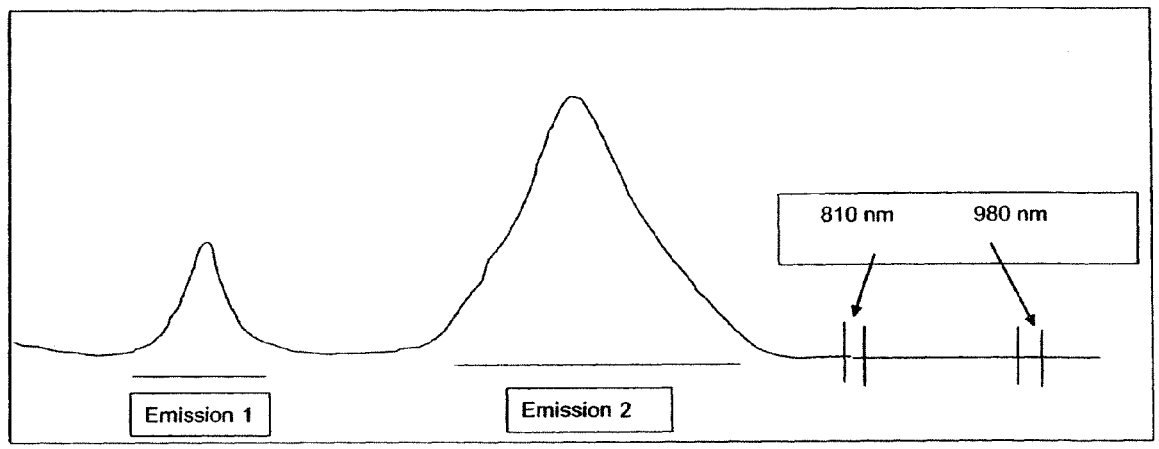
FIG. 4 is a graph showing diagrammatically the spectral analysis obtained by the method of the invention represented symbolically in FIG. 3.

The principle of image acquisition in accordance with the invention that is illustrated in FIG. 4 essentially consists in:

(i) exciting the fluorophore at the first excitation wavelength $\lambda_1$ and storing the transmission at the same wavelength $\lambda_1$;

(ii) storing either simultaneously, if an acquisition device with spectrum analysis is available, or successively, the emissions of fluorescence of this fluorophore at the two maximum wavelengths $\lambda'_1$ and $\lambda'_2$, and then (iii) repeating the above steps (i) and (ii) with the second excitation wavelength $\lambda_2$ applied to the same fluorophore.

The simplified calculations below show that the use in accordance with the invention of a plurality of excitation wavelengths $\lambda_1$ and $\lambda_2$ and emission wavelengths $\lambda'_1$ and $\lambda'_2$ produces much more information than prior art optical imaging methods, such as the FRI method, not only in respect of an estimate of the depth in direction Z of the fluorophores but also in respect of the mean absorption coefficients of the tissue.

To deduce the depth z of the fluorophore from the above-mentioned acquisition of the invention, additional measurements are advantageously available for the same number (5) of unknowns. We have:

I $(\lambda_1, \lambda'_1) = f(a_1, a'_1)$: measurement no. 1 with excitation at $\lambda_1$ and emission at $\lambda'_1$, $$I(\lambda_1, \lambda'_1) = I_1^0 \eta(\lambda_1, \lambda'_1) e^{-a_1(L-z)} e^{-a'_1 z}$$

I $(\lambda_1, \lambda'_2) = f(a_1, a'_2)$: measurement no. 2 with excitation at $\lambda_1$ and emission at $\lambda'_2$, $$I(\lambda_1, \lambda'_2) = I_1^0 \eta(\lambda_1, \lambda'_2) e^{-a_1(L-z)} e^{-a'_2 z}$$

I $(\lambda_2, \lambda'_1) = f(a_2, a'_1)$: measurement no. 3 with excitation at $\lambda_2$ and emission at $\lambda'_1$;

$$I(\lambda_2, \lambda'_1) = I_2^0 \eta(\lambda_2, \lambda'_1) e^{-a_2(L-z)} e^{-a'_1 z}$$

I ($\lambda_2$, $\lambda'_2$)=f($a_2$, $a'_2$): measurement no. 4 with excitation at $\lambda_2$ and emission at $\lambda'_2$;

$$I(\lambda_2, \lambda'_2) = I_2^0 \eta(\lambda_2, \lambda'_2) e^{-a_2(L-z)} e^{-a'_2 z}$$

ratio of the transmissions of the tissue at $\lambda_1$ and $\lambda_2$:
I ($\lambda_1$, $\lambda'_1$)/I($\lambda_2$, $\lambda'_2$)=f($a_1$, $a_2$): measurement no. 5

$$\frac{I(\lambda_1, \lambda'_1)}{I(\lambda_2, \lambda'_2)} = \frac{I_1^0}{I_2^0} e^{-(a_1-a_2)L}$$

Consequently, sufficient equations are available for solving the system with no a priori assumption as to the absorption coefficients, which can even be determined in the following very simple way.

The ratio of the transmissions of the different kinds of tissue (measurement no. 5) gives the difference ($a_1$–$a_2$) between the mean absorption coefficients at the excitation wavelengths, provided that the incident intensities $I_1^0$ and $I_2^0$ delivered by the excitation sources at $\lambda_1$ and $\lambda_2$, and the thickness L of the animal are known, which data can be measured experimentally.

The ratio of the emissions measured at $\lambda'_1$ (or at $\lambda'_2$) then gives the depth a of the fluorophore from the following equation, provided that the ratio of the emission quantum efficiencies at $\lambda'_1$ on excitation at $\lambda_1$ and $\lambda_2$ are known, which data is specific to the marker and measurable independently using a spectrofluorimeter:

$$\frac{I(\lambda_1, \lambda'_1)}{I(\lambda_2, \lambda'_1)} = \frac{I_1^0 \eta(\lambda_1, \lambda'_1) e^{-(a_1-a_2)(L-z)}}{I_2^0 \eta(\lambda_2, \lambda'_1)} = \frac{I(\lambda_1, \lambda_1)}{I(\lambda_2, \lambda_2)} \times \frac{\eta(\lambda_1, \lambda'_1)}{\eta(\lambda_2, \lambda'_1)} \times e^{(a_1-a_2)z}$$

If required, the difference ($a'_1$–$a'_2$) between the absorption coefficients at the emission wavelengths may be measured by the ratio of the emissions at $\lambda'_1$ and $\lambda'_2$ on excitation either at $\lambda_1$ or at $\lambda_2$:

$$\frac{I(\lambda_1, \lambda'_1)}{I(\lambda_1, \lambda'_2)} = \frac{\eta(\lambda_1, \lambda'_1)}{\eta(\lambda_1, \lambda'_2)} \times e^{-(a'_1-a'_2)z}$$

Note that the above calculations are excessively simplified, since they take no account of diffusion, which is very high at the wavelengths used, wherein a plurality of fluorescent sources may be present.

Figure 5:
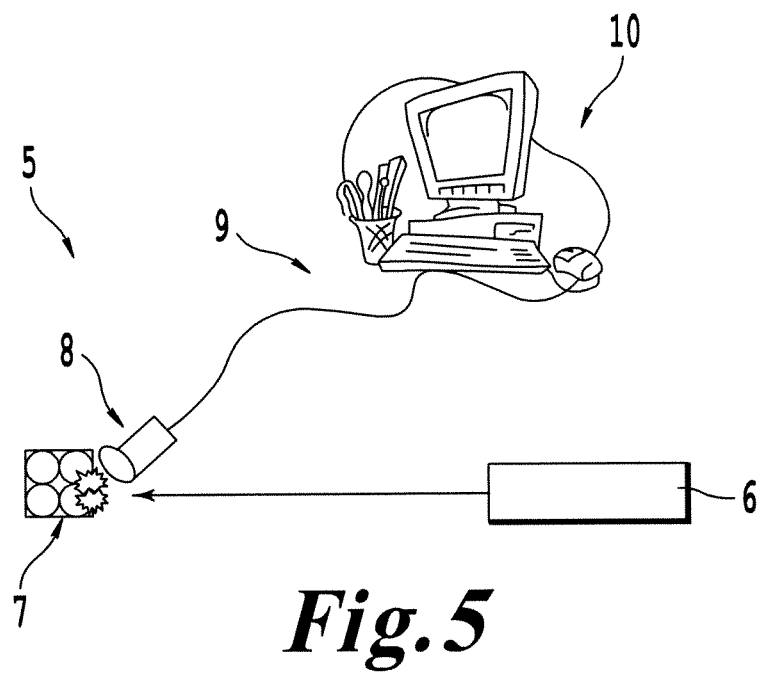
FIG. 5 is a diagram showing the essential elements of an optical characterization bench used in relation to fluorophores of the invention of the up-converting nanocrystal type.

2) Trials Highlighting the Optical Properties of Fluorophores in the Method of the Invention:

The optical characterization bench shown in FIG. 5 was used to highlight the emission properties of up-converting type oxide nanocrystals having the formula $Y_2O_3$: $Er^{3+}$,$Yb^{3+}$ used in the method of the invention (the nanocrystals tested are sold by the company DGTec). The different rates of doping with erbium (Er) and ytterbium (Yb) were studied, the rates each varying from 5% to 15%, and these nanocrystals were tested both in the powder state and in solution in a liquid mimicking the optical properties of the tissue.

This bench 5 essentially comprises:
a laser light source 6 adapted to emit radiation in the near infrared spectrum at excitation wavelengths $\lambda_1$ and $\lambda_2$ equal to 980 nm and 815 nm, respectively;
a sample 7 of $Y_2O_3$: $Er^{3+}$,$Yb^{3+}$ oxide nanocrystals;
a fiber 8 with XF 3100 filter adapted to capture the fluorescence emitted by the sample 7; and
a fiber spectrometer 9 connected to means 10 for acquiring and displaying the signals obtained.

These oxide powder nanocrystals were placed either directly in a spectrophotometer tank with a side length of 1 cm or in a 1 mm capillary tube placed in a tank filled with intra-lipid mimicking the optical properties of the tissue.

Figure 6A:
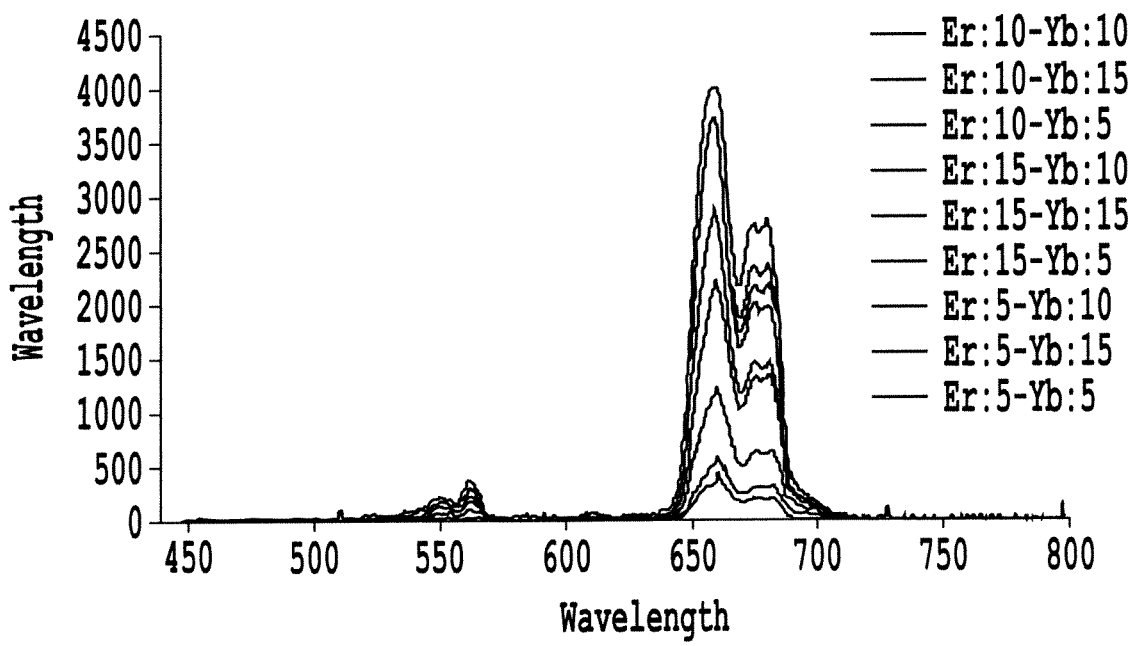
FIG. 6 is a graph showing the two emission bands obtained for those nanocrystals in the powder state on excitation at a first wavelength $\lambda_1$, including a detail view of the first of these emission bands.
Figure 6B:
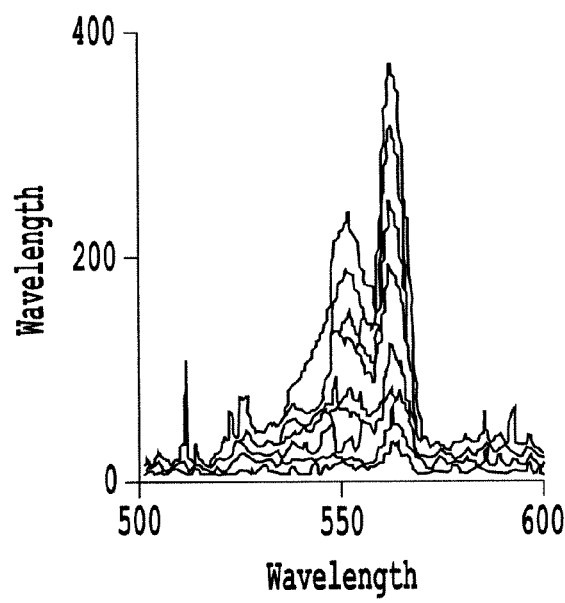
Figure 7A:
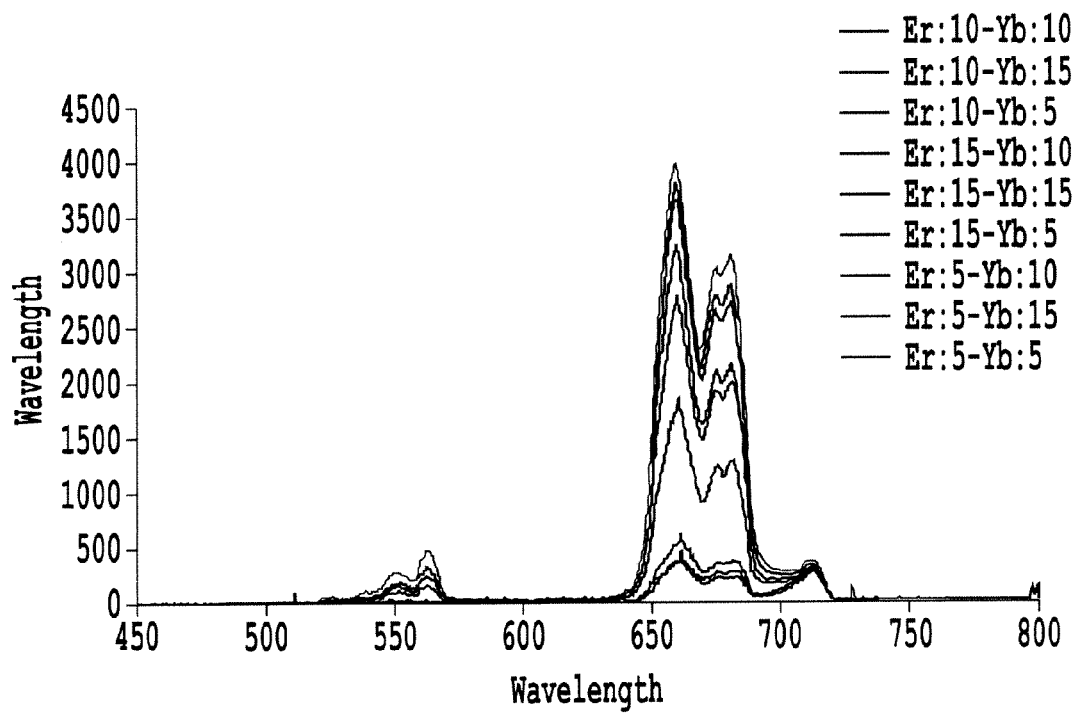
FIG. 7 is a graph showing the same two emission bands obtained for these nanocrystals in the powder state on excitation at a second wavelength $\lambda_2$, also including a detail view of the first of these two emission bands.
Figure 7B:
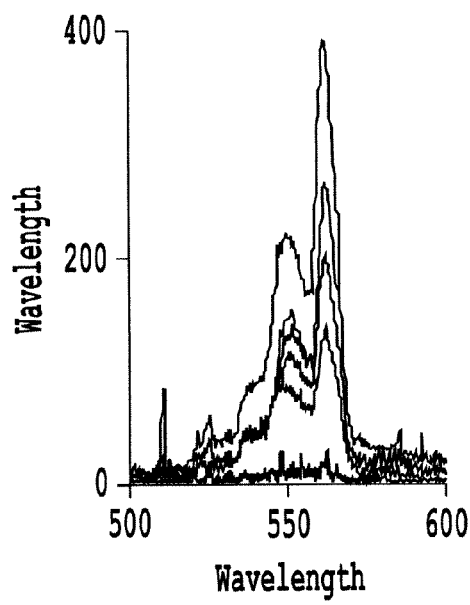

On separate excitation of the $Y_2O_3$: $Er^{3+}$,$Yb^{3+}$ nanocrystals in the powder state at the wavelengths $\lambda_1$=980 nm and $\lambda_2$=815 nm, two emission bands $B_1$ and $B_2$ were observed, namely green emission at $\lambda'_1$=560 nm and red emission of greater intensity at $\lambda'_2$=661 nm, as shown in FIGS. 6 and 7 respectively, which respectively relate to excitation at $\lambda_1$ and $\lambda_2$.

Figure 8A:
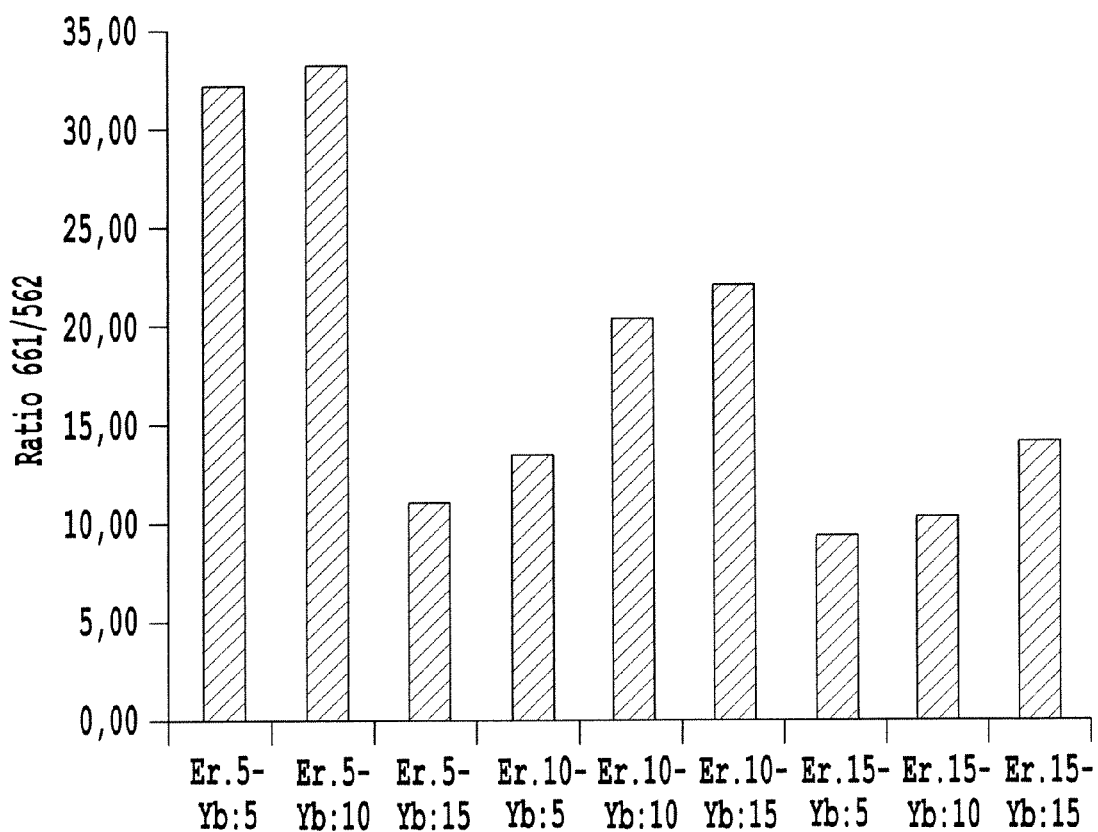
FIG. 8 contains two graphs respectively illustrating, for two excitation wavelengths $\lambda_1$ and $\lambda_2$, the ratios of fluorescence obtained for the two emission bands of FIGS. 6 and 7 as a function of the rates of doping of the ions used for these nanocrystals.
Figure 8B:
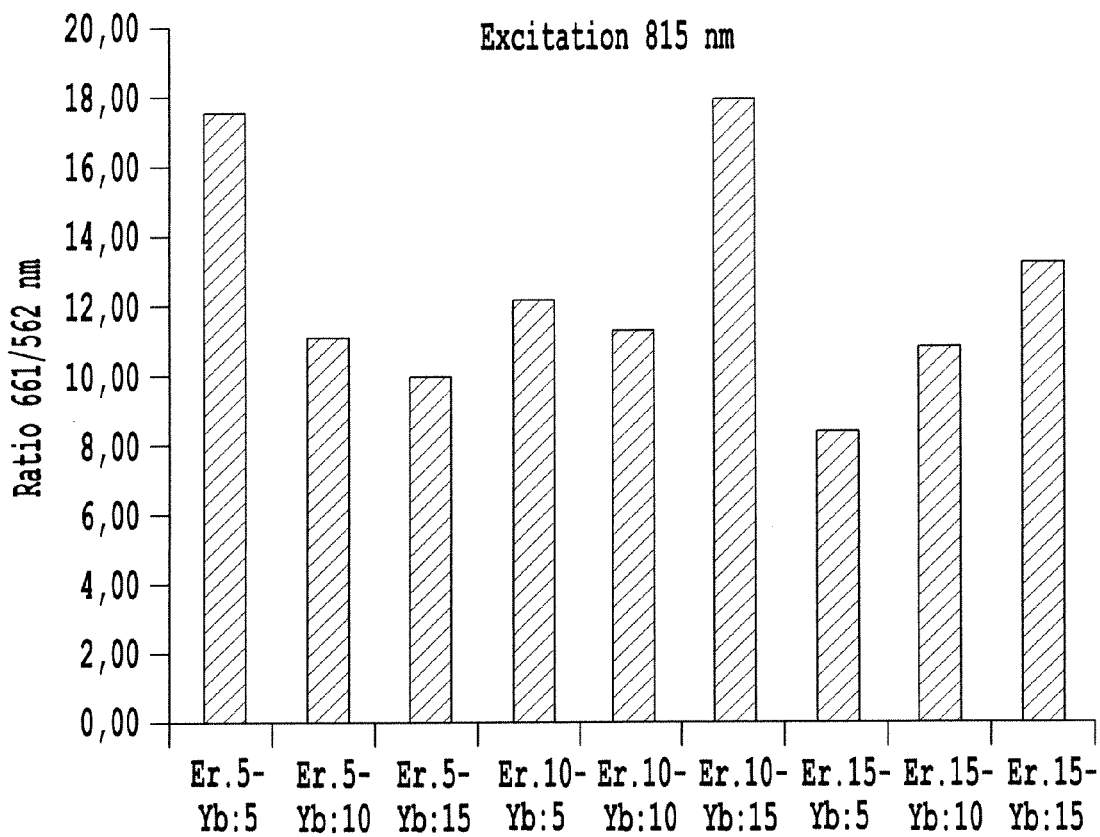

These different rates of doping with $Er^{3+}$ and $Yb^{3+}$ in combination yield fluorophores having different emission ratios between the band at $\lambda'_2$=661 nm and that at $\lambda'_1$=560 nm, as shown in the two bar charts of FIG. 8, which also refer to the same nanocrystals analyzed in the powder state (the same combined doping rates as shown in FIGS. 6 and 7 are used again on the abscissa axis in FIG. 8). These emission ratios also differ depending on the excitation wavelengths $\lambda_1$ and $\lambda_2$.

Although less intense than in the powder state, it was verified that these emission properties of the $Y_2O_3$: $Er^{3+}$,$Yb^{3+}$ nanocrystals, having doping rates of 10% for $Er^{3+}$, and 5% for $Yb^{3+}$, are preserved in a liquid medium having optical properties similar to those of the biological tissue, as shown in FIG. 9.

This liquid medium consists of an intra-lipid solution formed of 80% of a water-ink mixture and 20% of intra-lipid, to obtain an absorption coefficient $\mu_a$=0.05 cm$^{-1}$ and a reduced diffusion coefficient of $\mu'_s$=12 cm$^{-1}$, representative of biological tissue.

A 1 mm capillary tube was filled with these nanocrystals either in the powder state or in solution in water at different concentrations (10 grams per liter (g/L) and 1 g/L), and this capillary was placed at the center of a spectrophotometer tank with a side length of 1 cm filled with intra-lipid. Furthermore, an XF 3100 filter was used to eliminate diffusion in two tests of excitation in powder form and in solution effected at 815 nm.

Figure 9:
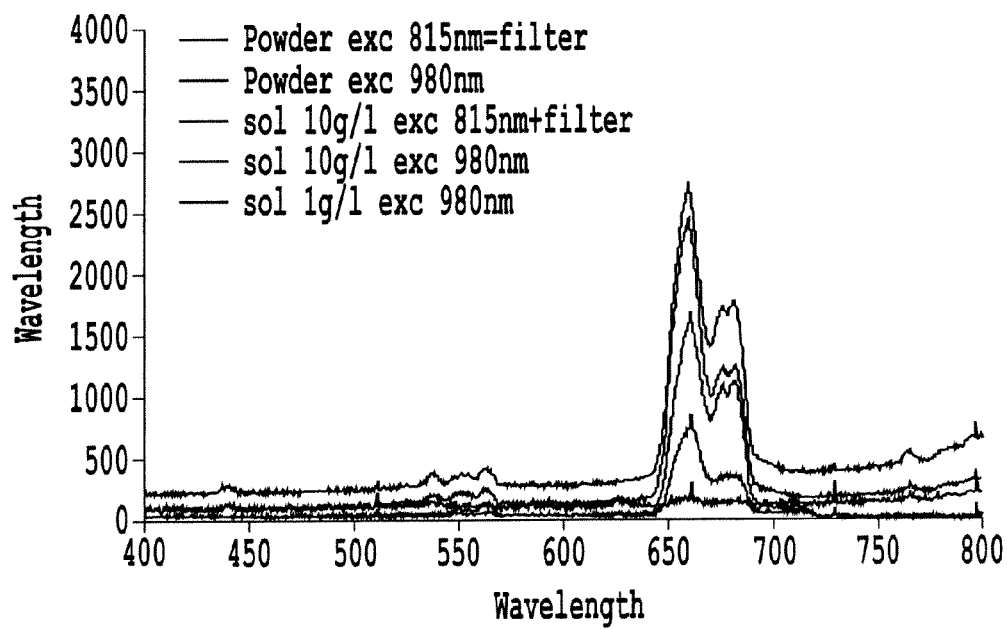
FIG. 9 is a graph showing the two similar emission bands obtained for these nanocrystals in the powder state or in solution in a liquid medium on excitation at the first or second wavelength $\lambda_1$ or $\lambda_2$, and with or without antidiffusion filters.
Figure 10A:
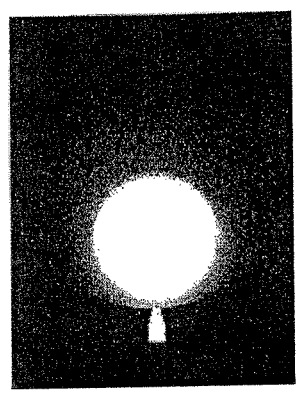
FIG. 10 shows fluorescence images obtained with the corresponding levels of grey, for the same nanocrystals deposited to different depths in an animal phantom, either in the powder state or at different concentrations in a liquid medium.
Figure 10B:
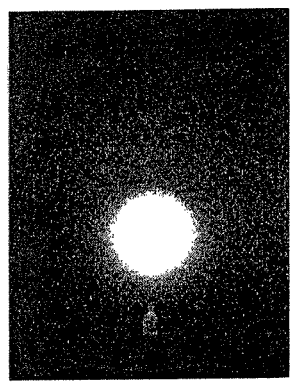
Figure 10C:
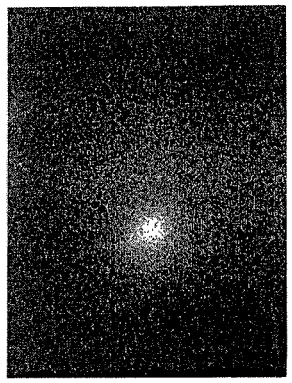
Figure 10D:
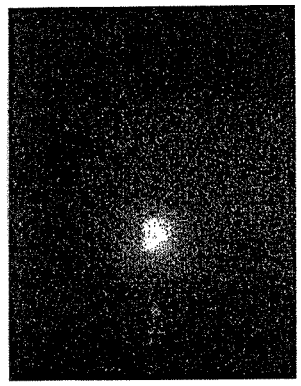
Figure 10E:
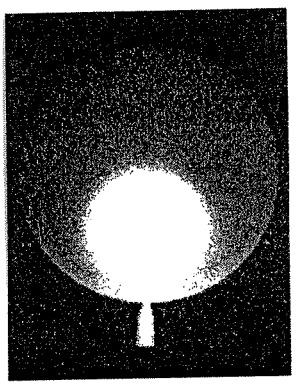
Figure 10F:
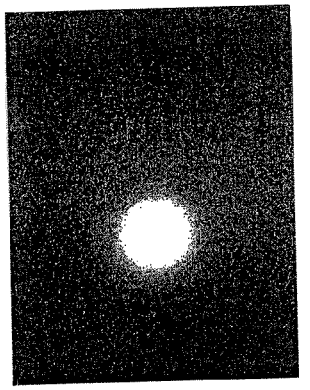

FIG. 9 shows that there is emission of fluorescence at 550 nm and 660 nm, i.e. substantially at the wavelengths $\lambda'_1$ and $\lambda'_2$ on excitation of the nanocrystals at $\lambda_1$=980 nm and $\lambda_2$=815 nm.

In conclusion, these fluorophores consisting of up-converting semiconductor inorganic nanocrystals satisfy well, both the condition of double sequential excitation at wavelengths $\lambda_1$ and $\lambda_2$ separated by more than 100 nm ($\lambda_1$–$\lambda_2$=165 nm) and the condition of simultaneous substantially identical emission of fluorescence for excitation at each of the wavelengths $\lambda_1$ and $\lambda_2$, conditions required for the implementation of the method of the invention.

Note that this double sequential excitation completely circumvents the problem of autofluorescence of the tissue, in particular by means of the up-converting properties of the oxide nanocrystals.

Note also that the two lines observed at 560 nm and 661 nm are very stable in position and that their relative intensity depends only on the proportions of the basic constituents. Moreover, no spectral offset was observed, whatever the environment.

The wavelength gap (approximately 100 nm) between the two emissions is sufficient for discriminating a fluorophore at depth from a surface fluorophore. In fact, a surface fluorophore sees the contribution of the line at 560 nm and that at 661 nm equally whereas, a contrario, a fluorophore at depth sees the contribution of the line at 560 nm as clearly less than that at 661 nm.

The use of up-converting inorganic nanocrystals also has the following advantages:

the excitation wavelengths can be chosen in a wide range, for example as a function of the tissue and/or the light source; in fact, $Y_2O_3$: 10% $Er^{3+}$, 5% Yb3+ nanocrystals can be excited at two wavelengths (815 nm and 980 nm) for which low-cost lasers are available off the shelf and that correspond to very good transmission of photons in the tissue;

autofluorescence of the tissue is eliminated or significantly reduced by means of the up-converting properties of these nanocrystals;

the problems of diffusion of the excitation light and filtering are limited by means of the significant differences between excitation and emission wavelengths (which avoids overlapping therebetween), the very fine absorption/emission lines, and the up-converting properties of the oxide nanocrystals of the invention;

these up-converting nanocrystals may be fabricated in nanometric sizes and are a priori non-toxic, being highly inert chemically under physiological conditions;

these nanocrystals feature very stable positioning of the emission and excitation lines, thus facilitating optical filtering; and these nanocrystals can be easily functionalized, with a view to targeting tissue or biological organs.

Concerning this point, different functionalization methods have been described for these nanocrystals with the object of introducing biological ligands, for example for recognizing overexpressed cellular receptors on the surface of tumor cells. Note that these methods are usable in the context of the invention.

3) Example of Application of the Method of the Invention:

The optical imaging method of the invention was used on a small animal, such as a mouse, for the detection of structures of interest (tumors, organs). To this end, markers were detected based on diverse samples of the above-mentioned inorganic nanocrystals with the formula $Y_2O_3$: 10% $Er^{3+}$, 5% $Yb^{3+}$ through a liquid mimicking the optical properties of the biological tissue of the animal.

A sample of these nanocrystals was placed in a closed capillary (1.5 mm diameter) and introduced into a phantom simulating a known biological medium ($\mu_a$=0.2 $cm^{-1}$ and $\mu'_s$=10 $cm^{-1}$). The capillary placed at different thicknesses of the phantom was lit from below by a 980 nm (30 mW) laser using the above-described tomography set-up shown in FIG. 2. The emission from these nanocrystals was recovered using a camera placed above the phantom.

More precisely, trials were carried out with these nanocrystals in 1 g/L solution (diagram d ), 10 g/L solution (diagrams a , b , c ) and powder (diagrams e and f ).

FIG. 10 shows the fluorescent emission images and the grey levels (NG) obtained for different concentrations of these nanocrystals.

This FIG. 10 shows that these nanocrystals with the formula $Y_2O_3$: 10% Er, 5% Yb in 10 g/L solution in a capillary are easily detectable in the phantom to a depth up to 4 mm, this penetration depth advantageously enabling visualization of all the organs of a small animal such as a mouse. Note further the high diffusion that exists at these wavelengths in a medium mimicking the optical properties (diffusion, absorption) of the tissue.

What is claimed is:

1. A method of optically imaging at least one biological tissue, the method comprising:
    a) introducing at least one fluorescent marker into said at least one tissue;
    b) exciting said at least one marker by incident light radiations and detecting bands of emission relating to fluorescence emitted by said at least one marker in response to that excitation; and
    c) analyzing intensities of fluorescence relative to said emission bands,
    wherein the step b) includes,
        sequentially exciting said at least one marker at n different incident excitation wavelengths $\lambda_i$, said at least one marker excitable by at least two of these n wavelengths $\lambda_i$ and to emit in response to each wavelength $\lambda_i$ a series $S_i$ of m simultaneous emission bands $B_j$ having m different maximum wavelengths $\lambda'_j$ that are substantially same from one series $S_i$ to another (where n and m are independent integers equal to or greater than 2 and where i and j respectively vary from 1 to n and from 1 to m), and
        detecting at least two of the series $S_i$ that each comprise the m bands $B_j$ emitted simultaneously in order to deduce therefrom in the step c) at least one of an estimate of a three-dimensional location of said marker in the at least one tissue and mean absorption coefficients of the at least one tissue for the excitation wavelengths $\lambda_i$.

2. An imaging method according to claim 1, wherein said at least one marker is based on a fluorophore or a group of fluorophores that is excitable by the incident excitation wavelengths $\lambda_i$ and that emits the m bands $B_j$ simultaneously in response to each of the incident excitation wavelengths $\lambda_i$.

3. An imaging method according to claim 1 or 2, wherein the step c) also comprises determining one or more emission ratios between the m maximum wavelengths $\lambda'_j$ and one or more transmission ratio(s) of said at least one tissue between the n different incident excitation wavelengths $\lambda_i$, to obtain an emission map of said at least one tissue.

4. An optical imaging method according to claim 1 or 2, wherein the method further comprises using an optical imaging device operating in transmission mode and including a source of incident radiations and a detector which are situated on respective both opposite sides of said at least one tissue.

5. An optical imaging method according to claim 1 or 2, wherein the method further comprises using an optical imaging device including a source of incident radiations and a detector both of which are situated on a same side of said at least one tissue.

6. An optical imaging method according to claim 5, wherein the step b) further comprises deducing a backscattering map of the at least one tissue at the n different incident excitation wavelengths $\lambda_1$.

7. An optical imaging method according to claim 1 or 2, wherein the n different incident excitation wavelengths $\lambda_i$ are offset in pairs by an interval of at least 100 nm.

8. An optical imaging method according to claim 1 or 2, wherein the m maximum wavelengths $\lambda'_j$ of said emission bands $B_j$ are offset in pairs by an interval of at least 100 nm.

9. An imaging method according to claim 1 or 2, wherein the n different incident excitation wavelengths $\lambda_i$ are all of between 750 nm and 1000 nm.

10. An imaging method according to claim 9, wherein the m maximum wavelengths $\lambda'_j$ of said emission bands $B_j$ are all of between 450 nm and 800 nm.

11. An optical imaging method according to claim 1 or 2, wherein the step b) comprises:
  successively exciting said at least one marker at two different excitation wavelengths $\lambda_1$ and $\lambda_2$, said at least one marker being adapted to be excited by these two wavelengths $\lambda_1$ and $\lambda_2$ and to emit in response substantially same series $S_1$, $S_2$ of two emission bands $B_1$ and $B_2$ having respective different maximum wavelengths $\lambda'_1$ and $\lambda'_2$ (n=m=2); and
  detecting the two series $S_1$ and $S_2$ each comprising the two bands $B_1$ and $B_2$ emitted simultaneously.

12. An imaging method according to claim 1 or 2, wherein the at least one marker comprises a fluorophore based on at least one up-converting semiconductor inorganic nanocrystal.

13. An imaging method according to claim 12, wherein said nanocrystal includes at least:
  an oxide or an oxysulfide of a metal selected from a group consisting of yttrium, vanadium and rare earth elements; and
  an emitter ion, which is a rare earth cation.

14. An imaging method according to claim 1, wherein said at least one marker further comprises an element chosen from a group consisting of chelates of gadolinium, nanoparticles of oxides of iron and nanoparticles of gadolinium, which element makes said at least one marker act as a contrast agent usable in magnetic resonance imaging, positron emission tomography, gammatomography or X-ray imaging.

15. An imaging method according to claim 13, wherein said nanocrystal is based on an yttrium oxide having a formula $Y_2O_3$: $Er^{3+}$, $Yb^{3+}$, where Er and Yb are respectively erbium and ytterbium and each is present in said nanocrystal at a doping rate from 1% to 20%.

16. An imaging method according to claim 1 or 2, wherein said at least one tissue is in vivo, said at least one marker is based on a fluorophore and biological ligand conjugate, which is an up-converting semiconductor nanocrystal and biomolecule conjugate.

17. An imaging method according to claim 1 or 2, wherein the step c) includes generating at least one of an emission map, absorption map, and backscattering map to define at least one region of interest of said at least one tissue to be analyzed by tomography.

18. An imaging method according to claim 17, further comprising using said at least one region of interest of said at least one tissue as a starting point for image reconstruction by tomography.

19. An imaging method according to claim 17, wherein said at least one of the emission map, absorption map, and backscattering map relates to an entire animal body.

* * * * *